(12) United States Patent
Lebrun et al.

(10) Patent No.: US 12,195,456 B1
(45) Date of Patent: Jan. 14, 2025

(54) SINGLE MOLECULES HAVING MIXED CDK4, CDK6, PLK1 TARGETING PROPERTIES

(71) Applicants: Jean-Jacques Lebrun, Montreal (CA); Bertrand Jean-Claude, Montreal (CA); Karine Pasturaud, Paris (FR); Suhad Ali, Montreal (CA)

(72) Inventors: Jean-Jacques Lebrun, Montreal (CA); Bertrand Jean-Claude, Montreal (CA); Karine Pasturaud, Paris (FR); Suhad Ali, Montreal (CA)

(*) Notice: Subject to any disclaimer, the term of this patent is extended or adjusted under 35 U.S.C. 154(b) by 164 days.

(21) Appl. No.: 17/066,824

(22) Filed: Oct. 9, 2020

Related U.S. Application Data

(60) Provisional application No. 62/913,666, filed on Oct. 10, 2019.

(51) Int. Cl.
C07D 471/04 (2006.01)
A61K 31/496 (2006.01)
A61P 35/00 (2006.01)

(52) U.S. Cl.
CPC ............ C07D 471/04 (2013.01); A61P 35/00 (2018.01)

(58) Field of Classification Search
CPC .. C07D 471/02; C07D 471/04; A61K 31/496; A61K 31/519; A61P 35/00
USPC .......................... 544/279; 514/252.16, 258.1
See application file for complete search history.

(56) References Cited

U.S. PATENT DOCUMENTS 11,225,492 B2 * 1/2022 Zhang ..................... A61P 35/02

* cited by examiner

Primary Examiner — Charanjit Aulakh

(57) ABSTRACT

A series of molecules designed to block CDK4/CDK6, with preferentially stronger inhibitory potency against CDK4 is described. The identification of a lead molecule with triple CDK4, CDK6 and PLK1-targeting potency is disclosed.

9 Claims, 15 Drawing Sheets

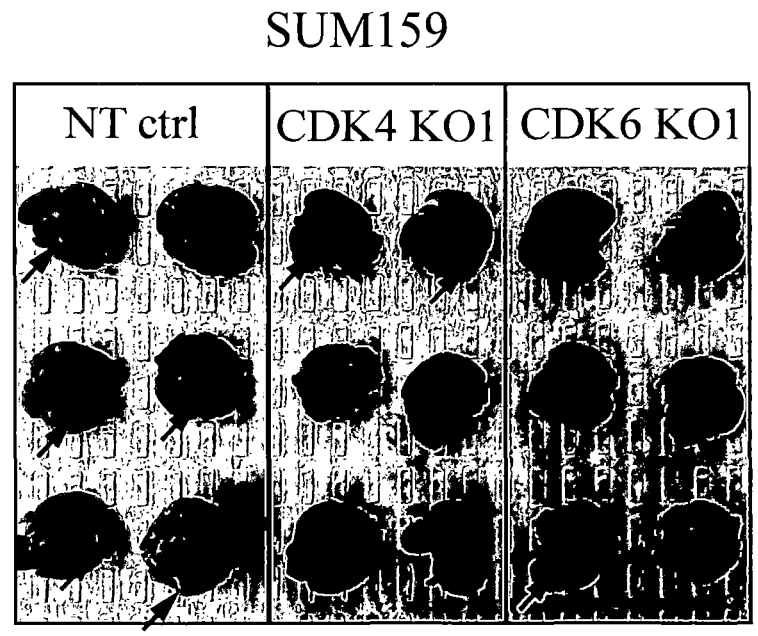
FIG.1 : CDK4/6 CRISPR knockout effects on lung metastasis.
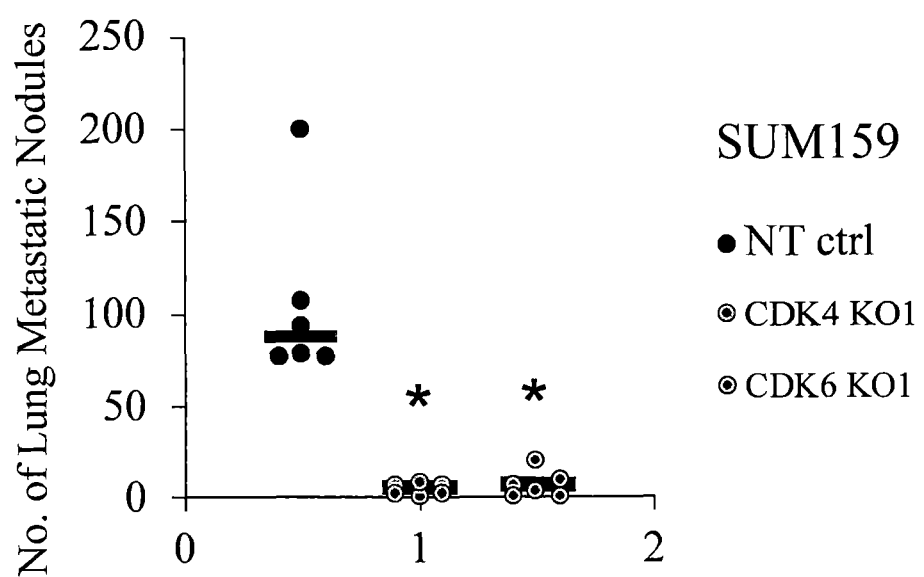
FIG.2 : Quantification.

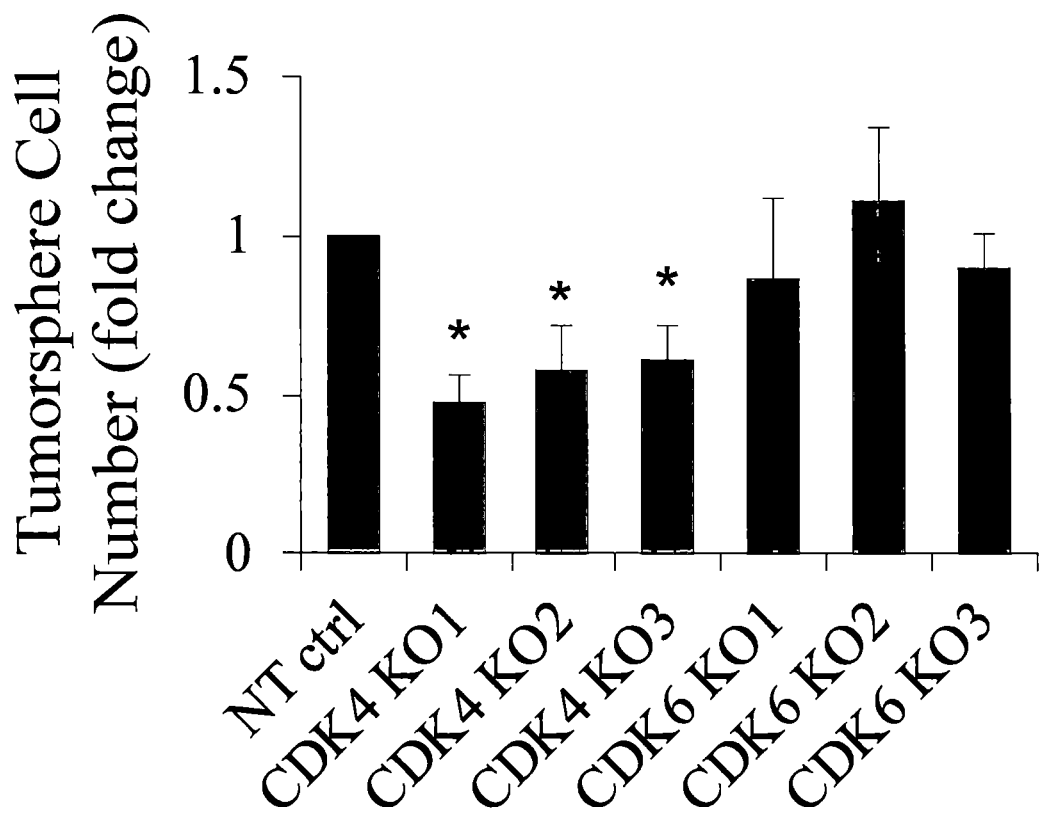
FIG.3 : CDK4/6 CRISPR knockout effects on tumorsphere formation.

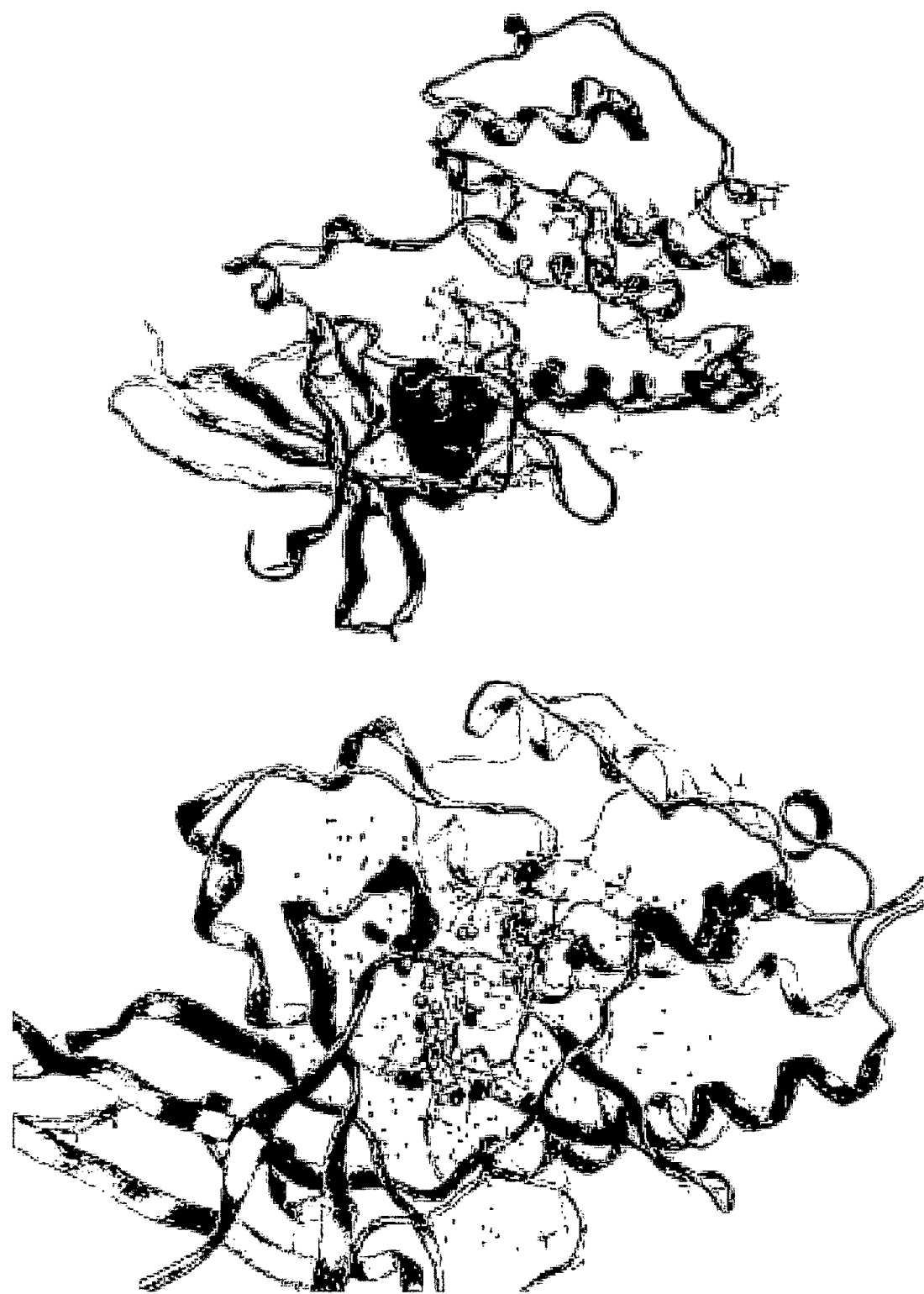
FIG.4 : X-Ray crystal structure of CDK6 with palbociclib (PDB codes: ID 3G33 and 5L2I) used for MOE modeling.

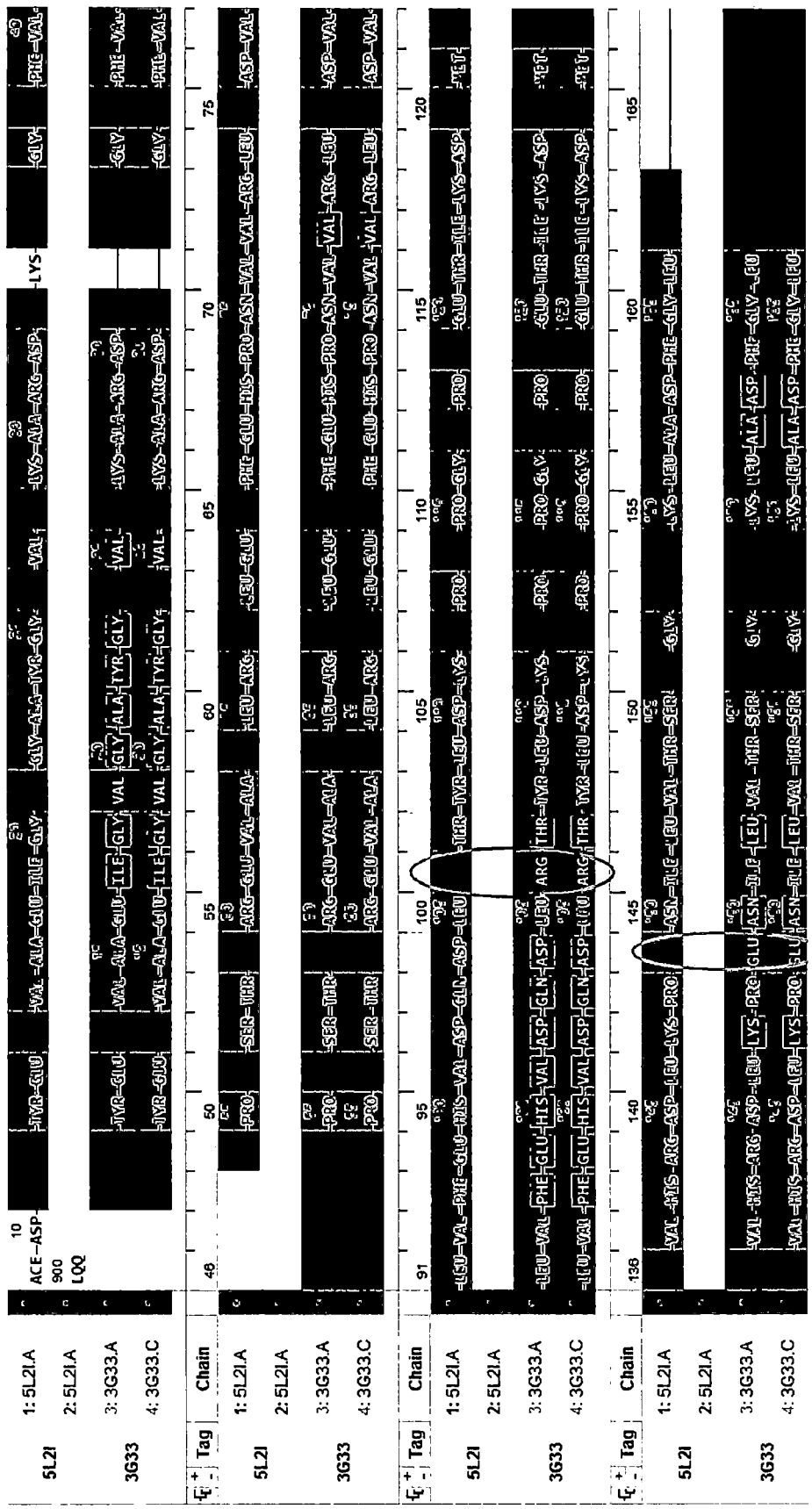
FIG.5: Protein sequence alignment between CDK4 (3G33) and CDK6 (5L2I). Active pocket sites are in blue with CDK4/6 differences circled in yellow.

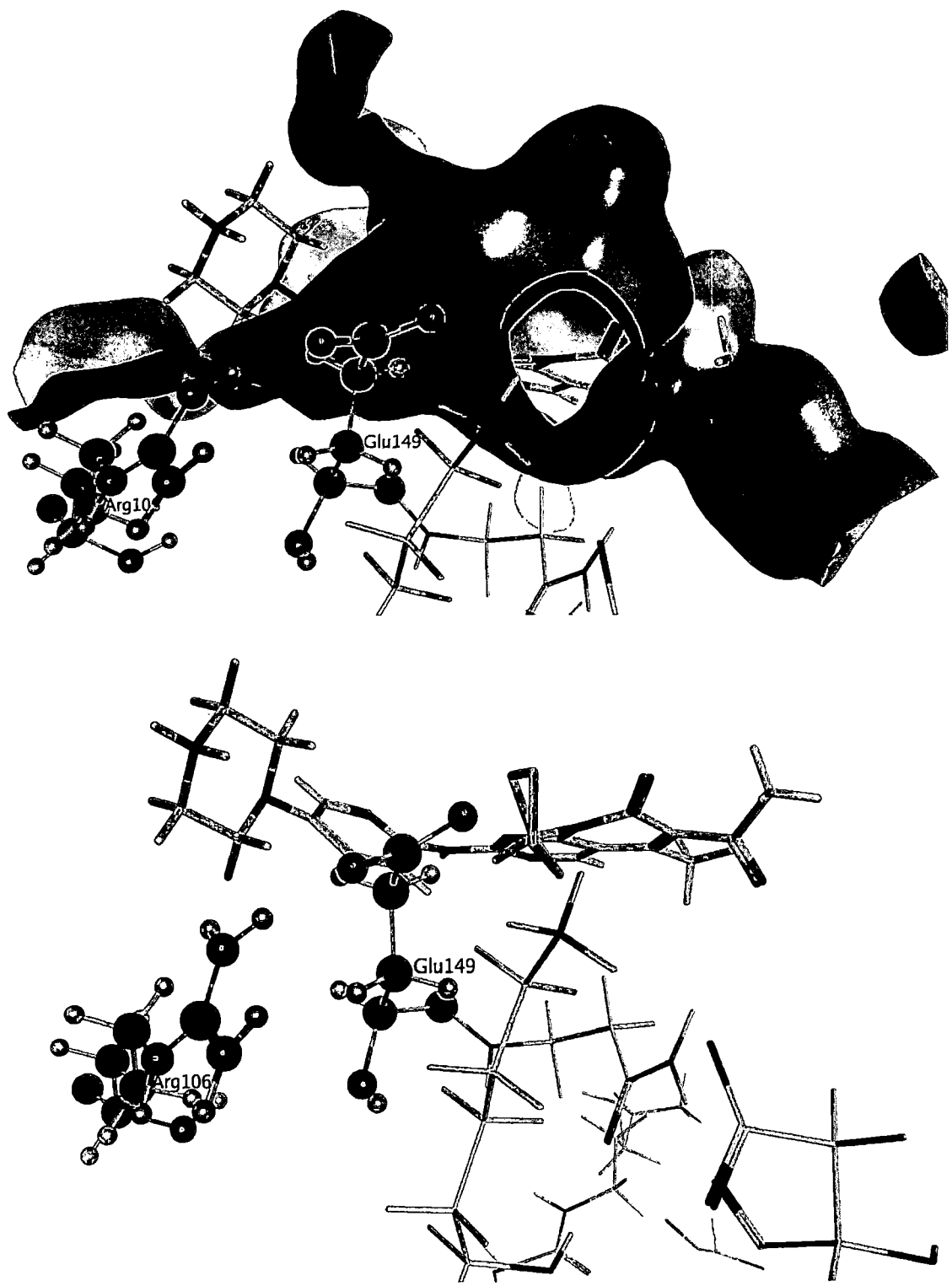
FIG.6 : CDK4 interaction with palbociclib.

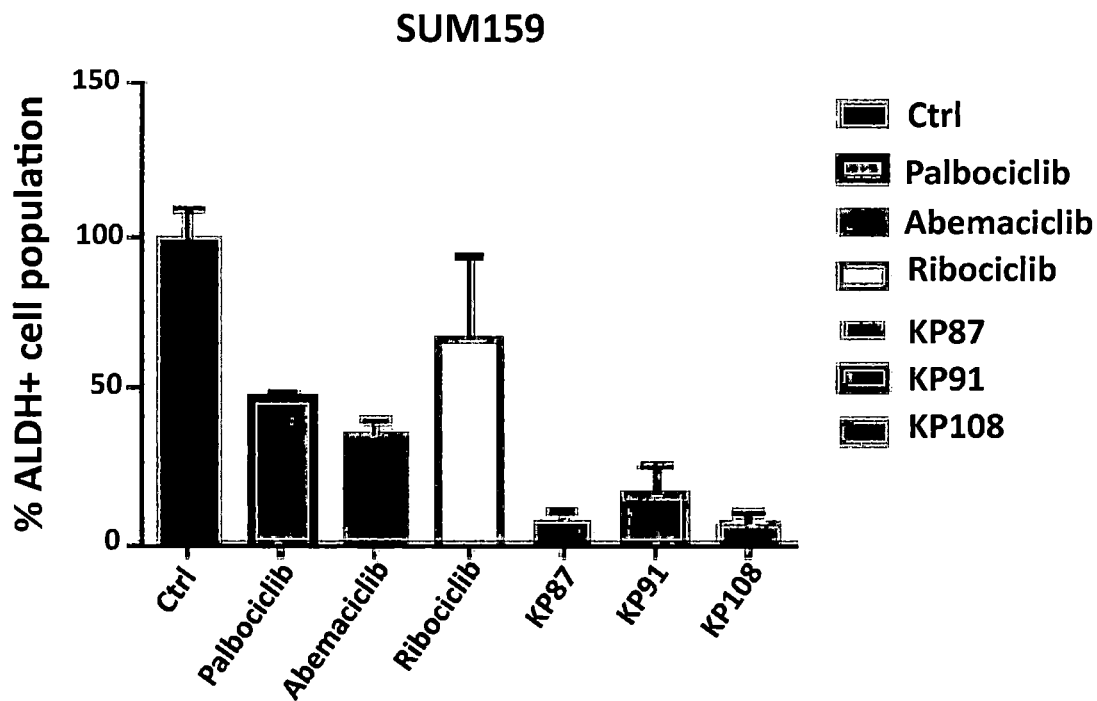
FIG.7 : CDK4 inhibitors effects on cancer stem cells in SUM159.
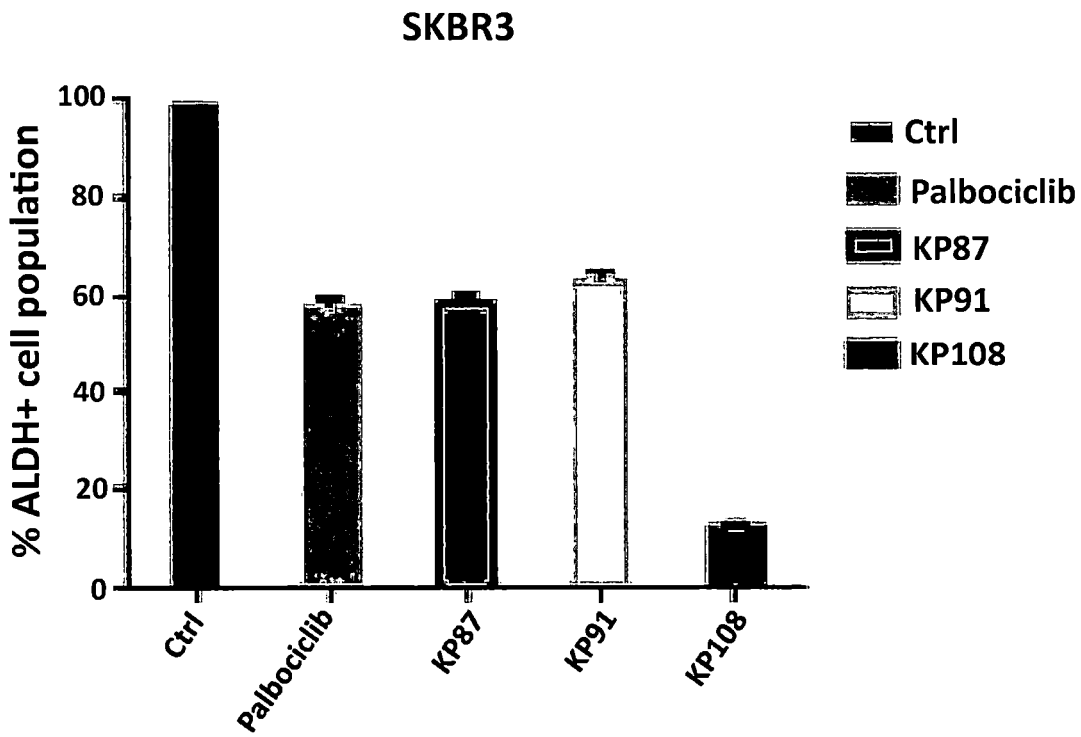
FIG.8 : CDK4 inhibitors effects on cancer stem cells in SKBR3.

| Compound | CDK4/D | CDK6/D | Selectivity between CDK4 and CDK6 |
|---|---|---|---|
| KP108 | 0.77 | 20.4 | 26 |
| Palbociclib | 9 | 15 | 1.7 |
| Abemaciclib | 5 | 10 | 2 |
| Ribociclib | 10 | 39 | 3.9 |

FIG.9: CDK4/6 IC50 (nM)

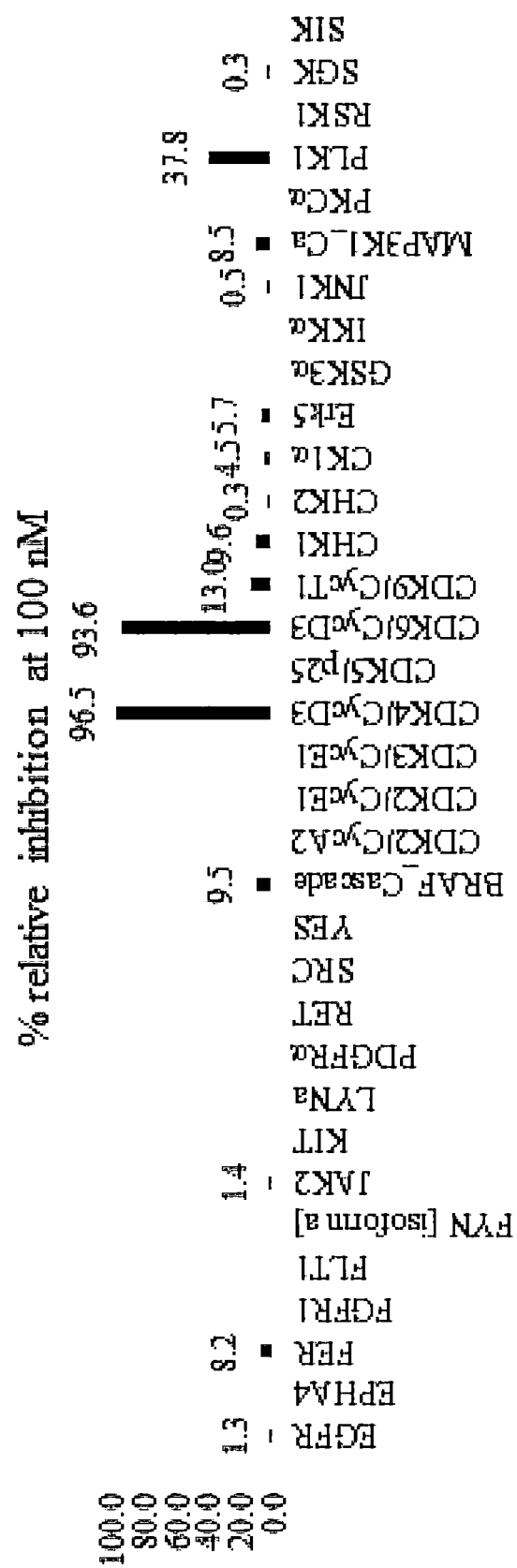
FIG.10 : KP108 kinase profiling.

| Inhibitor | Affinity kcal/mol | No of bonds | Strength bond force | Distance Å from main residue | Functional group |
|---|---|---|---|---|---|
| Palbociclib | -226.5586 | 5 | -12.3 | 1.71 Lys40 | -CO |
| | | | -0.70 | 2.33 Asp163 | CH3-CO |
| | | | -4.4 | 2.02 Val101 | =N3- |
| | | | -1.3 | 1.99 Val101 | -N2-H |
| | | | -1.0 | 2.12 Glu149 | -NH- |
| KP108 | -233.9424 | 6 | -12.3 | 1.71 Lys40 | -CO |
| | | | -0.7 | 2.33 Asp163 | CH3-CO |
| | | | -4.4 | 2.02 Val101 | =N3- |
| | | | -1.3 | 1.99 Val101 | -N2-H |
| | | | -3.2 | 1.83 Glu149 | -NH- |
| | | | -3.3 | 2.09 Arg106 | -CO |

FIG.11 : KP108/PLK1 binding predictions.

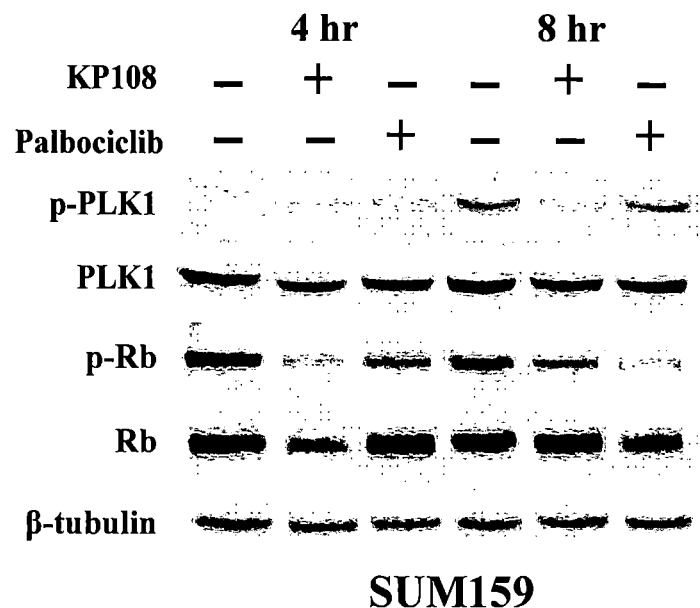
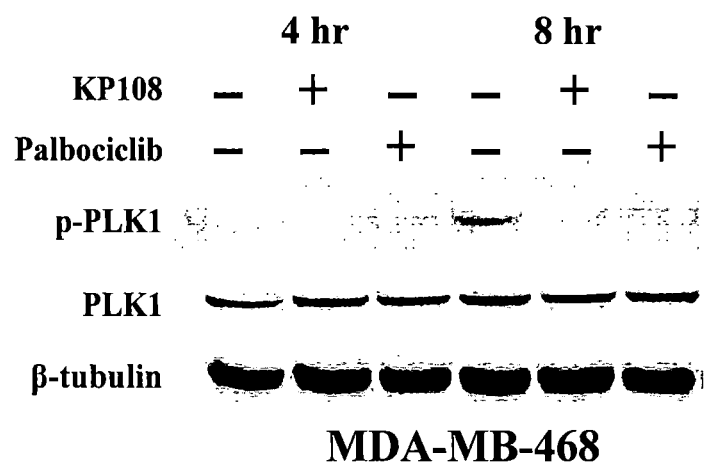
FIG.12 : PLK1/Rb phosphorylation status.

| Compound | PLK1 | PLK2 | PLK3 | PLK4/SAK |
|---|---|---|---|---|
| KP108 | 360 | >10000 | - | 2000 |

FIG.13: KP108 IC50 (nM)

| Cell line | Tumor type | KP108 IC$_{50}$ (uM) | Palbociclib IC$_{50}$ (uM) |
|---|---|---|---|
| SUM159 | breast (triple negative) | 0.27 | 0.20 |
| SUM149 | breast (triple negative) | 0.29 | 7.1 |
| MDA-MB-468 | breast (triple negative), RB-deficient | 0.46 | 3.4 |
| MDA-MB-231 | breast (triple negative) | 0.54 | 10.9 |
| SKBR3 | HER2+ | 0.21 | 12.7 |
| SPC2 | bone metastasis (from MDA-MB-231) | 0.31 | 3.06 |
| PC3 | prostate | 0.50 | 7.0 |
| HPAF-II | pancreas | 1.3 | 18.4 |
| BX-PC3 | pancreas | 0.78 | 16.03 |

FIG.14: KP108/Palbociclib IC50 comparison in a panel of human tumor cell lines

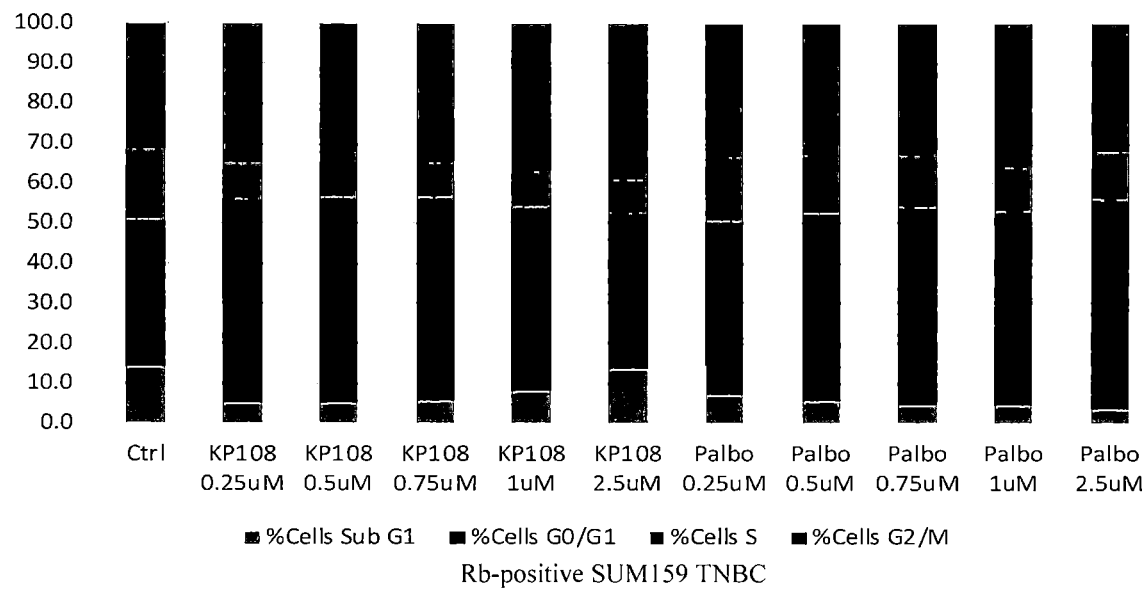
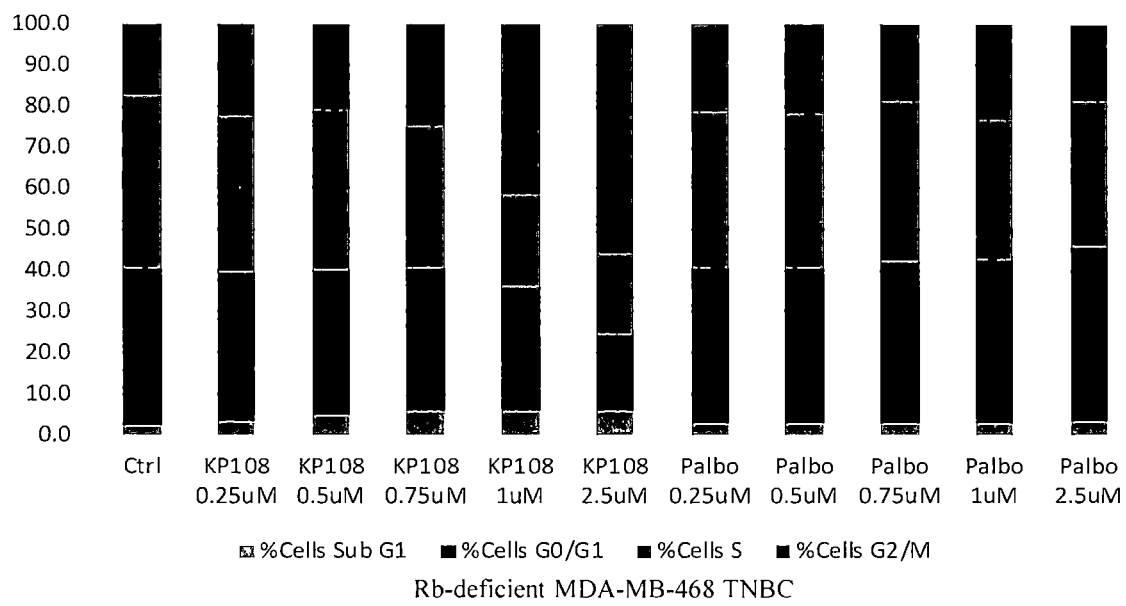
FIG.15 : KP108/palbociclib effects on cell cycle.

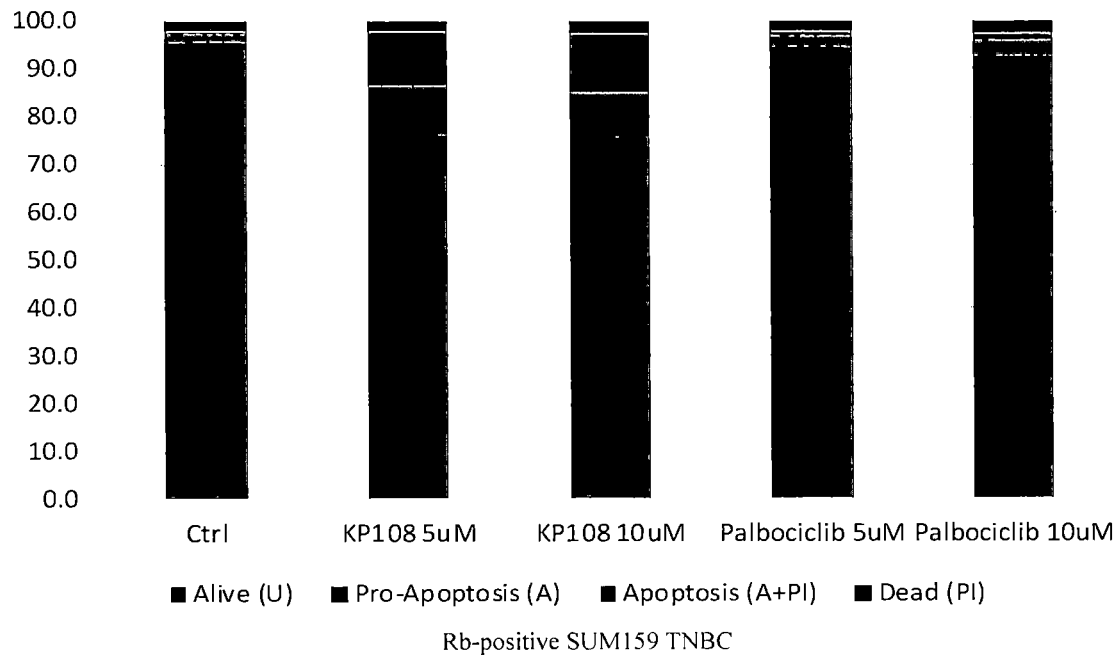
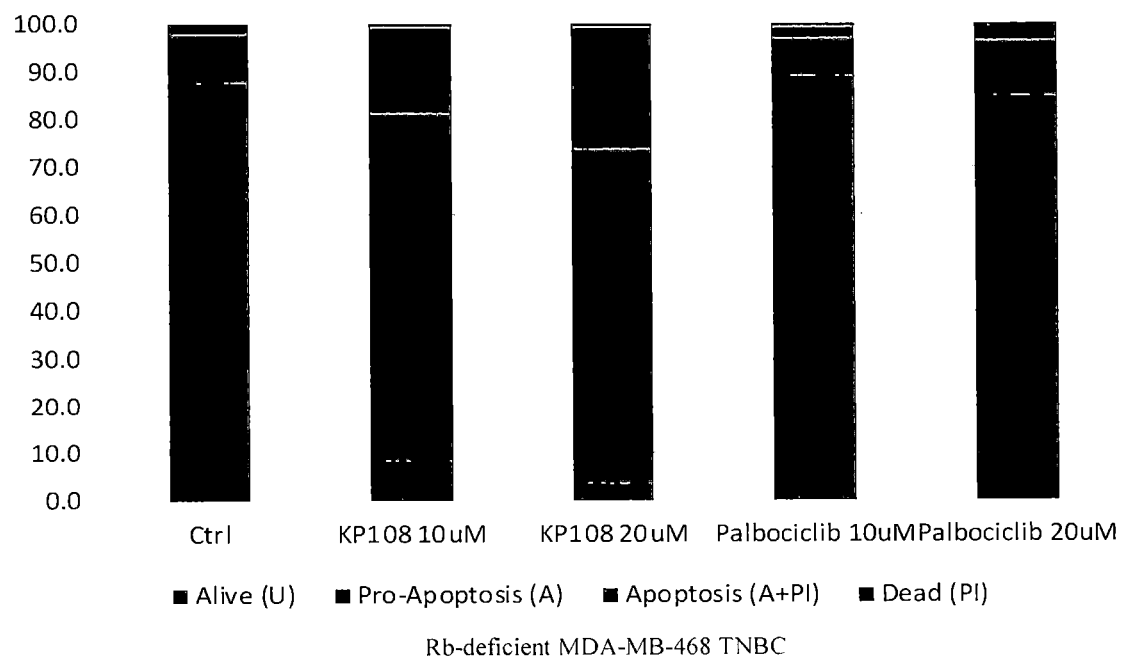
FIG.16 : KP108/palbociclib effects on apoptosis.

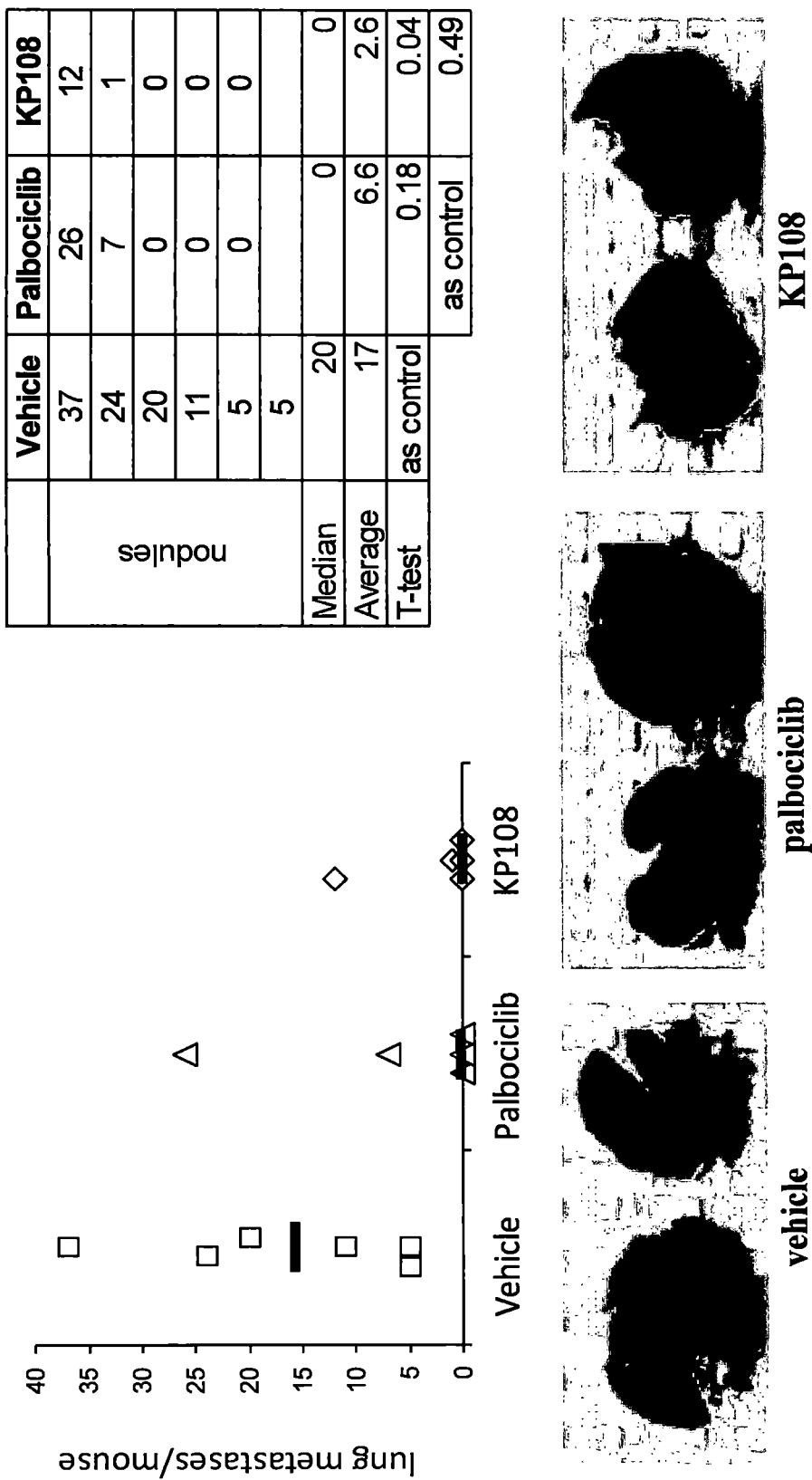
FIG.17: KP108/palbociclib effects on lung metastasis (preclinical model of intravenous injection).

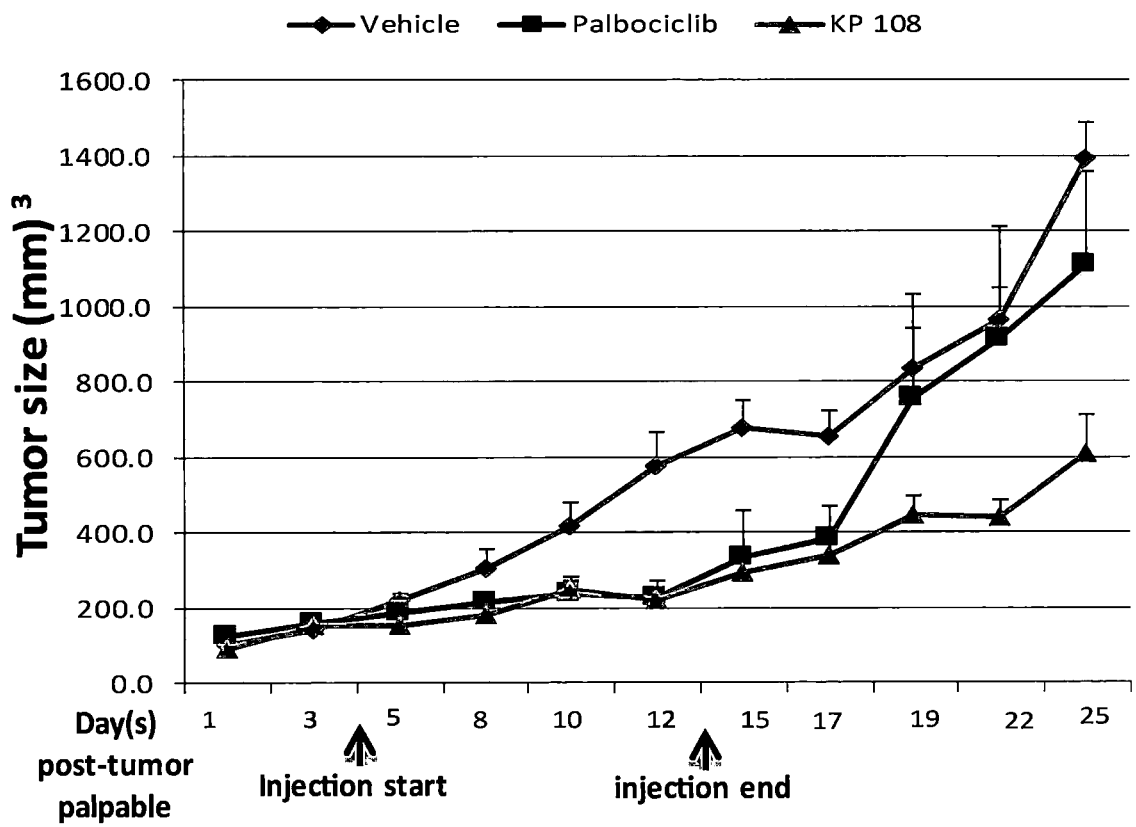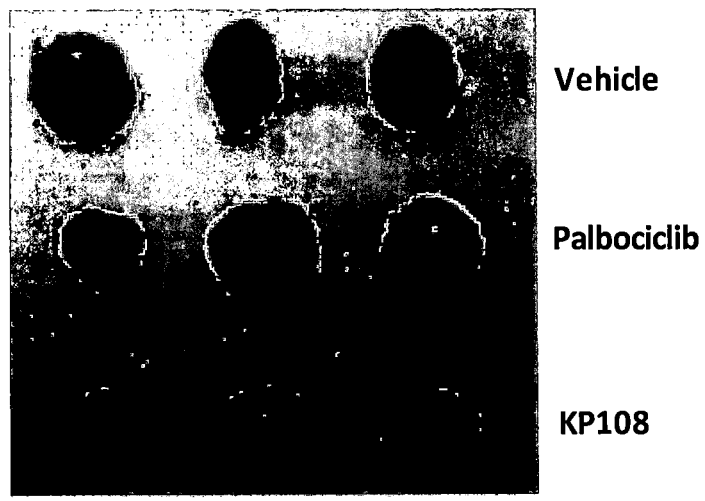
FIG.18 : KP108/palbociclib effects on primary tumor growth (preclinical model of orthotopic transplantation).

SINGLE MOLECULES HAVING MIXED CDK4, CDK6, PLK1 TARGETING PROPERTIES

FIELD

The current disclosure broadly relates to agent designed to preferentially block CDK4 over CDK6 with the purpose of killing breast cancer stem cells and prevent resurgence.

BACKGROUND

Breast cancer is the most common cancer in women worldwide with 30% of patients relapsing with distant metastases[1]. Metastatic disease remains the leading cause of death in these patients accounting for 90% of all cancer-related deaths[1-3]. Triple negative breast cancer (TNBC) and human epidermal growth factor receptor 2-positive (HER2+) are the most aggressive breast cancer molecular subtypes. Poor prognosis, high metastasis rates, tumor recurrence and relapse in these metastatic tumors are driven by populations of cancer stem cells (CSCs), which utilize their self-renewal ability to drive continued expansion of malignant cells, tumor relapse and resistance to chemotherapy[4,6].

To date, there are no approved treatments or effective therapies targeting CSCs in these types of tumors nor any approved targeted treatments for TNBC, highlighting a clear medical gap and unmet clinical need for these deadly tumors. The critical need for anti-CSC therapies is underlined by the twenty or so currently active or recruiting clinical trials in the breast cancer/CSC field (clinicaltrials.gov). A search for breast cancer and cancer stem cell revealed 146 clinical trials, of which only 18 are currently active or recruiting (34 including those with unknown status), the rest being suspended, terminated, completed or withdrawn.

We recently made inroads into understanding cancer stem cell biology in breast cancer and found high expression of the cyclin-dependent kinase 4 (CDK4) to correlate with poor overall and relapse-free survival outcomes in metastatic TNBC patients[6]. We further showed that silencing CDK4, but not the closely related kinase CDK6, efficiently reduced CSC numbers and reversed the basal TNBC mesenchymal phenotype to an epithelial- and luminal-like phenotype, highlighting CDK4 as a promising therapeutic target in CSC-enriched breast metastatic tumors[6].

While existing pan-CDK4/6 inhibitors (i.e. Pfizer palbociclib) showed promising results on primary tumor growth when used in combination therapy in hormone receptor positive (HR+) tumors[7], they failed clinical trials for TNBC. This is likely due to the fact that 1)—half of TNBCs are Rb-deficient (CDK4/6 target) and thus will escape anti-CDK4/6 therapies; 2)—these inhibitors equally target CDK4 and CDK6, whereby blocking CDK6 does not affect cancer sternness and 3)—they elicit very limited efficacy against CSCs in TNBCs (see attached figures).

We hypothesized that designing new kinase inhibitors to more selectively target CDK4 and perhaps other kinases may lead to eradication of CSCs, thereby paving the way for novel effective targeted therapy for metastatic breast cancers as well as other cancers enriched in CSC populations.

Using structure-based and molecular modeling approaches, with the scaffold of the clinical approved drug palbociclib, we generated a series of novel CDK4 inhibitors named the KP series. Over 100 small molecule inhibitors were synthesised and assessed in vitro for their anti-CSC activities, leading to the identification of several promising hit-to-reads (KP87, 91, 108).

We identified KP108, our current lead candidate that showed over 10-fold greater inhibition of CDK4 compared to palbociclib, along with a clear superior efficacy in targeting CSCs in vitro in metastatic breast cancer cells. Interestingly, when screening against a panel of 50 kinases, we found KP108 to exert a dual targeting activity and to efficiently inhibit the Polo-like Kinase-1 (PLK1).

While known as a key regulator of the G2-M phase of the cell cycle, new emerging functions for PLK1 have recently been uncovered in tumor metastasis[8,9], thus providing an attractive added value for KP108 and further expanding its potential tumor growth inhibitory capacity. Moreover, we found KP108 to be very active in other solid tumor types (i.e. prostate and pancreatic cancers). Thus, while initially targeting the breast cancer therapeutic area, with a proposed specific indication for metastatic HER2+ and TNBC tumors, KP108 would also benefit other metastatic cancer types. Finally, using in vivo preclinical models of breast cancer; we found KP108 to exhibit great efficacy and sustained activity in blocking both primary tumor formation and metastasis in orthotopic transplantation and intravenous tail vein injection models, respectively.

The current disclosure refers to documents the content of which is incorporated herein by reference in their entirety

SUMMARY

The current disclosure related to single molecules capable of blocking CDK4, CDK6 and/or PLK1 with the purpose of killing stem cells in triple negative breast cancer and other solid tumors, thereby preventing recurrence In an embodiment, the current disclosure relates to molecules of Formula I or a pharmaceutically acceptable salt thereof:

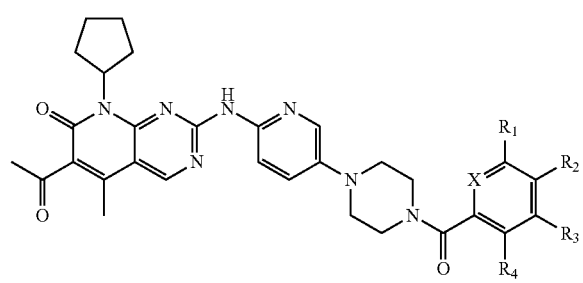

I wherein:
R1 is selected from a group consisting of H, $NO_2$, $NH_2$, $CF_3$
R2 is selected from a group consisting of H, $NH_2$, NHMe, N(Me)CONHOH, COOMe, $NHCONHCH_2CH_2Cl$, $N(Me)CONHCH_2CH_2Cl$
R3 is selected from a group consisting of H, $NH_2$, NHMe, N(Me)CONHOH, $NHCONHCH_2CH_2Cl$, $N(Me)CONHCH_2CH_2Cl$
R4 is selected from a group consisting of H, F, Cl, Br, NO2, Me
X is selected from a group consisting of C or N,
In an embodiment, the current disclosure relates to molecules of Formula I or a pharmaceutically acceptable salt thereof:

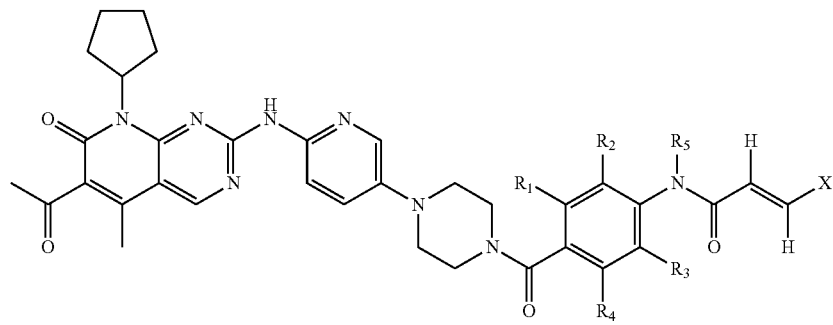

II wherein:
R1 is selected from a group consisting of H, F, Cl, Br, NO2, Me
R2 is selected from a group consisting of H, F, Cl, Br, NO2, Me
R3 is selected from a group consisting of H, F, Cl, Br, NO2, Me
R4 is selected from a group consisting of H, F, Cl, Br, NO2, Me
R5 is selected from a group consisting of H, Me, Et, Propyl
X is selected from a group consisting of H, Me, ethylmorpholine, propylmorpholine, —CH$_2$—N(CH$_3$)$_2$, CH$_2$CH$_2$N(CH$_3$)$_2$ In another embodiment, the current disclosure relates molecules of Formula II or a pharmaceutically acceptable salt thereof:

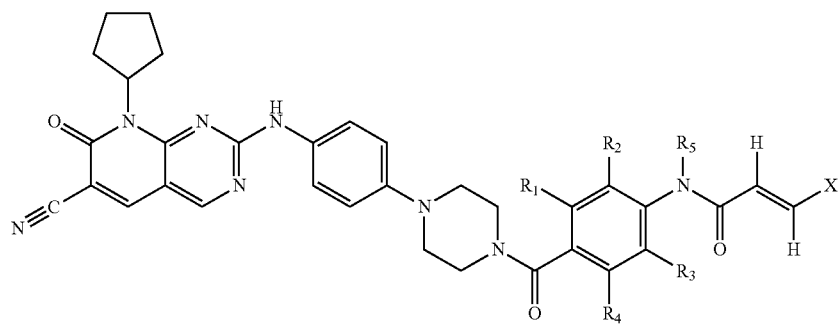

III wherein:
R1 is selected from a group consisting of H, F, Cl, Br, NO2, Me
R2 is selected from a group consisting of H, F, Cl, Br, NO2, Me
R3 is selected from a group consisting of H, F, Cl, Br, NO2, Me
R4 is selected from a group consisting of H, F, Cl, Br, NO2, Me
R5 is selected from a group consisting of H, Me, Et, Propyl
X is selected from a group consisting of H, Me, alkylmorpholine, —CH$_2$—N(CH$_3$)$_2$, CH$_2$CH$_2$N(CH$_3$)$_2$

BRIEF DESCRIPTION OF DRAWINGS

FIG. 1 shows—(LEFT) CRISPR/Cas9 CDK4 knockouts, using 3 single guide RNAs induces a significant reduction in lung metastatic nodules, compared to scramble knockouts. (RIGHT) Tumorsphere assays were used to determine the effect of specific CDK4 and CDK6 knockouts on the CSC frequency. Results from 1,000 cell seeding indicate that blocking CDK4 but not CDK6 inhibits tumorsphere formation *p<0.05

FIG. 2 shows Effects of our hit-to-leads (KP87, KP91, KP108) compared to existing CDK4/6 inhibitors (palbociclib, abemaciclib, ribociclib) on ALDH+ cancer stem cell numbers at equimolar concentrations in triple negative breast cancer (left) and HER2+ (right) breast cancer cells.

Table 1 shows the IC50 (nM) of KP108 and existing CDK4/6 inhibitors against CDK4/cyclin D3 and CDK6/cyclin D3.

FIG. 3 shows the X-Ray crystal structure of CDK6 with palbociclib

FIG. 4 shows the X-Ray crystal structure of CDK6 with palbociclib (PDB codes: ID 3G33 and 5L2I) used for MOE modeling.

FIG. 5 shows the CDK4 and CDK6 sequence alignment.

FIG. 6 shows the CDK4 interaction with palbociclib using MOE computer modelization) sequence alignment.

FIG. 7 shows the effects of our hit-to-lead compounds (KP87, KP91, KP108) compared to existing CDK4/6 inhibitors (palbociclib, abemaciclib, ribociclib) on ALDH+ cancer stem cell numbers, at equimolar concentrations in triple negative breast cancer cells (SUM159).

FIG. 8 shows the effects of our hit-to-lead compounds (KP87, KP91, KP108) compared to existing CDK4/6 inhibitors (palbociclib, abemaciclib, ribociclib) on ALDH+ cancer stem cell numbers at equimolar concentrations HER2+ breast cancer cells (SKBR3).

FIG. 9 shows the IC50 (nM) of KP108 and existing CDK4/6 inhibitors against CDK4/cyclin D3 and CDK6/cyclin D3.

FIG. 10 shows the kinase profiling of KP108 against 50 kinases at 100 nM.

FIG. 11 shows the KP108/PLK1 bindng predictions.

FIG. 12 shows inhibition of phopsho-PLK1 and phosphor-Rb by KP108 and palbociclib in two triple negative breast cancer cell lines, SUM159 and MDA-MB-468.

FIG. 13 shows the IC50 (nM) of KP108 against the different PLK family members highlighting the specificity of KP108 aqainst PLK1.

FIG. 14 shows the effects of KP108 and palbociclib in cell lines representing different models of solid tumors. KP108 shows a lower IC50in all tumor types tested, includinq breast, prostate and pancreatic cancers.

FIG. 15 shows the effect of KP108 and palbociclib on cell cycle proqression aqainst the MDA-MB-468 and SUM159 TNBC cell lines. While both compounds induce G1 arrest in Rb-positive cells, only KP108 efficiently induce G2 arrest in Rb-deficient cells.

FIG. 16 shows the KP108 and palbociclib effects on apoptosis in Rb-positive SUM159 (upper panel) and Rb-deficient MDA-MB-468 (lower panel) TNBC cell lines. Only KP108 exerts a significant pro-apoptotic effect in both TNBC cells lines.

FIG. 17 shows the in vivo efficacy of KP108 and palbociclib against breast tumor metastasis following intravenous injection of SUM159 in a preclinical lung metastasis model (tail vein injection).

FIG. 18 shows the in vitro efficacy of KP108 and palbociclib against breast tumor SUM159 TNBC xenografts, before, during and following injections of the various compounds (vehicle, palbociclib, KP108).

DETAILED DESCRIPTION

In order to give a consistent understanding of the terms used in the present specification, definitions are provided below. Unless specified otherwise, all scientific and technical terms as used herein have the same meaning as commonly understood by one of ordinary skill in the art to which this invention belongs.

The use of "a" or "an" when in conjunction with the term "comprising" in the claims and/or the specification may mean "one". However, but it also means "one or more", "at least one", and "one or more than one". Likewise, the word "another" may mean at least a second or more.

Words and terms used in this specification and claim(s), such as "comprising" (and any form of comprising, such as "comprise" and "comprises"), "having" (and any form of having, such as "have" and "has") are inclusive and do not exclude unrecited elements or process steps. Words and terms used in this specification "including" (and any form of including, such as "include" and "includes") or "containing" (and any form of containing, such as "contain" and "contains"), are considered and defined as inclusive or open-ended and do not exclude any additional, unrecited elements or process steps.

The term "derivative" as used herein, is understood as being a substance that includes the same basic carbon skeleton and carbon functionality in its structure as a given compound but can also carry one or more substituents or rings.

The term "analogue" as used herein, is a substance, the structure of which does not comprise the same basic carbon skeleton and carbon functionality as a "given compound". However, the structure can mimic the given compound by incorporating one or more appropriate substitutions The term "salt(s)", is understood as being acidic and/or basic salts formed with inorganic and/or organic acids or bases. Zwitterions (internal or inner salts) are defined as being included within the term "salt(s)", as are quaternary ammonium salts such as alkylammonium salts.

The term "pharmaceutically acceptable salts" include the acid addition and the base salts of the structures in the present disclosure. Non-limiting acid addition salts are formed from acids which form non-toxic salts and such examples are the hydrochloride, hydrobromide, hydroiodide, tartrate, sulphate, fumarate, bisulphate, nitrate, phosphate, gluconate, hydrogen phosphate, maleate, acetate, lactate, citrate, succinate, benzoate, saccharate, methanesulphonate (i.e. mesylate), ethanesulphonate, benzenesulphonate, p-toluenesulphonate and pamoate salts.

The term "alkyl" can be branched or straight-chain. Examples of alkyl residues containing from 1 to 6 carbon atoms are methyl, ethyl, propyl, butyl, pentyl, hexyl, the n-isomers of ail these residues, isopentyl, isobutyl, isopropyl, neopentyl, 3-methylpentyl isohexyl, sec-butyl, tert-butyl, or tert-pentyl.

The definitions of selected terms are provided for clarity and consistency. However, the present description refers to a number of chemical terms and abbreviations used by those skilled in the art.

We initially found that silencing the cyclin-dependent kinase CDK4 gene expression through CRISPR/Cas knock-out (KO) efficiently reduced lung metastasis in vivo (FIG. 1A). Using an in vitro tumorsphere assay to quantify the CSC frequency of a breast cancer cell culture, grown in growth factor enriched serum free media, we also found that CDK4 KO Jed to a significant reduction in sphere forming efficiency, while CDK6 KOs failed to reproduce this effect, suggesting distinct functions for CDK4 and 6 (FIG. 1B).

Consistent with this, we found that silencing CDK4, but not CDK6 could reduce CSC numbers and reverse the basal TNBC mesenchymal phenotype to an epithelial- and luminal-like phenotype 6. Moreover, we also found showed that CDK4 and CDK6 have distinct transcriptomes and showed they regulate tumorigenesis and metastasis through distinct pathways, cancer sternness being more specifically regulated by CDK4[10].

We used structure-based and computational modelling approaches to design selective CDK4 inhibitors. Using X-ray crystal structures obtained from the protein data bank (PDB codes: ID 3G33 and 5L2I) and molecular modeling (Molecular Operating Environment MOE.2016 software), we used the palbociclib scaffold as an effective platform to add new functional groups that could favor interactions with CDK4 over CDK6. As there is no existing inhibitor/CDK4 X-ray cocrystal structure available, we used the X-ray cocrystal of palbociclib/CDK6 ATP binding pocket (5121) as a template to model the palbociclib scaffold within the X-ray crystal structure of CDK4/cyclin D3 (3G33) (FIG. 4). The high amino acid similarity between the two CDKs (68%) allowed us to confidently predict the CDK4 ATP-binding pocket structure.

Overlapping the CDK4 pocket with the CDK6 sequence revealed that the two pockets only differ by 2 amino-acid residues (Thr[106] and Gln[146] in CDK6 are replaced by Arg[106] and Glu[149] in CDK4) (FIG. 5, FIG. 6)). Interestingly, these two amino-acids are specific to CDK4, not found in any other CDK family members' and are located at the entrance of the ATP-binding pocket, facing the piperazine moiety of the core palbociclib structure. Thus, we used the piperazine free base as our core modified template to introduce various chemical functions, predicted to favor and create new binding interactions between the core structure and CDK4-specific amino-acids ($Arg^{106}$ and $Glu^{149}$). We designed, synthesized and prepared more than one hundred compounds (KP series), which were assessed for their ability to target CSCs and regulate tumorsphere formation in vitro.

Three compounds (KP87, 91 and 108) showed superior efficacy in reducing tumorsphere formation and were selected as hit-to-leads. The compounds were then assessed for their ability to reduce the ALDH+ CSC population, found in breast cancer and compared to existing CDK4/6 inhibitors (palbociclib, ribociclib and abemaciclib) at equimolar concentrations. Flow cytometry was used to measure the ALDH+ CSC numbers, as previously described[6,11-13]. Interestingly, all three compounds showed significant superior efficacy in eliminating ALDH+ CSCs in two different molecular subtypes of breast cancer, TNBC (SUM159) and HER2+ (SKBR3), particularly compound KP108 which showed nearly maximal efficacy in all models (FIG. 7(4), FIG. 8). As a result, KP108 was further selected as the first lead compound.

In vitro kinase assays revealed KP108 to exhibit a great $IC_{50}$ for CDK4 (0.77 nM), compared to palbociclib, ribociclib and abemaciclib ($IC_{50}$=9, 10 and 5 nM respectively) (FIG. 9). Not only did KP108 exhibit an eleven-fold superior inhibition of CDK4 activity compared to palbociclib but it is also 26 times more selective to CDK4 than CDK6 (IC50 CDK6=20.4 nM), whereas others CDK4/6 inhibitors did not show preferential selectivity between CDK4 and CDK6. Thus, our modification of the piperazine moiety succeeded in generating a highly selective CDK4 inhibitor with a lowered affinity for CDK6. Concomitantly, our data also demonstrated KP108 to be extremely efficient in eliminating CSC in different molecular subtypes of breast cancer, further validating our hypothesis.

We next analyzed KP108 potential off-target effects and binding affinity, using a panel of 50 different kinases, representative of different kinase families. Interestingly, we found no or little cross-reactivity, even at concentrations in the 100 nM range, except for the Polo-like kinase 1 (PLK1), highlighting PLK1 as a potential KP108 target and suggesting a dual kinase-like activity for KP108 (FIG. 10, FIG. 11). As expected, at these high concentrations, the relative % of inhibition is saturated at nearly 100% for both CDK4 and CDK6. To validate CDK4/6 and PLK1 as functional KP108 targets, we then assessed CDK4-mediated Rb phosphorylation (Ser780) and PLK1-mediated autophosphorylation (Thr210) in vitro.

Using immunoblotting with phospho-specific antibodies, we found our lead to efficiently block phosphorylation of both substrates in a time-dependent manner in TNBC cells. These results confirmed KP108 as a dual target inhibitor (FIG. 12). As PLK1 is overexpressed in 80% of metastatic breast cancers and the fact that it acts by blocking the G2-M phase of the cell cycle, this provides an attractive added value for KP108, further expanding its potential tumor growth inhibitory capacity.

We next analyzed KP108 effects on other PLK family members and found that KP108 only targets PLK1 (FIG. 13).

As PLK1 is overexpressed in 80% of metastatic breast cancers and the fact that it acts by blocking the G2-M phase of the cell cycle, this provides an attractive added value for KP108, further expanding its potential tumor growth inhibitory capacity.

KP108 also showed great activity in cellulo when tested in other TNBC cells (SUM149, MDA-MB-231) as well as in the Rb-deficient MDA-MB-438 cell line (FIG. 14). This is very interesting as 40% of TNBCs are Rb-deficient (CDK4 target), leaving existing CDK4/6-targeting therapies inefficient in almost half of the TNBC cases[14,15]. As such, current approved CDK4/6 inhibitors are not indicated for TNBC. On the contrary, by targeting PLK1 and the G2-M phase of the cell cycle, KP108 would be active in both Rb+ and Rb-deficient tumors and thus, have the potential to be indicated for all TNBCs. Consistent with this, we found Rb-deficient TNBC cells treated with KP108 to exhibit a dose-dependent increase in the G2 phase while cells treated with palbociclib remained in the G1 phase following initial synchronisation (FIG. 15).

We found that unlike palbociclib, KP108 exerts pro-apoptotic activities in TNBC. These effects are particularly strong (leading to almost complete cell death) in Rb-deficient TNBC cells (MDA-MB-468) (FIG. 16).

Our preliminary in cellulo testing also revealed KP108, but not palbociclib, to be very active in prostate and pancreatic cancers, further expanding its potential clinical use to other solid tumor types FIG. 14.

We previously showed that cyclins and CDK4/6 regulate CSC self-renewal and contribute to TNBC tumor formation and metastasis[6,16,17]. Consistent with this, palbociclib was found to partially reduce the metastatic burden in a patient-derived xenograft model of breast cancer[16]. To then functionally assess our lead in a preclinical model of tumor metastasis, immune-deficient non-obese diabetic scid gamma (NSG) mice were injected intravenously with $10^6$ TNBC cells. One week after (to allow for the seeding of cancer cells to the lungs) mice received daily I.P. injections of vehicle, KP108 or palbociclib at 50 mg/kg for another 2 weeks before being) sacrificed. Lungs were collected and stained with Bouin's solution and, the numbers of lung metastatic nodules were quantified.

KP108 showed great efficacy in vivo and significantly prevented, to almost completely block lung colonization (FIG. 17). In contrast, palbociclib only showed partial effect (not reaching significance when compared to control animals). We further assessed our compound on breast cancer tumorigenesis in vivo, through orthotopic transplantation of SUM159 TNBC cells into the mammary fat pad of NSG mice. Following transplantation of the cells (6 mice/group), tumors were allowed to grow until palpable before beginning a treatment regimen with KP108, palbociclib or control vehicle. Drugs were administered through i.p. daily injections for two weeks (50 mg/kg) and tumor volumes were measured, as per our team optimized protocol[10,19].

KP108 showed great efficacy in preventing primary tumor development. More surprisingly, and very interestingly, KP108 growth inhibitory effects sustained over time, even once injections were stopped (FIG. 18). In comparison, tumors from palbociclib treated animals immediately recovered and regrew quickly once the injections stopped. Moreover, unlike in mice, treated with palbociclib which showed weight loss, and significant health deterioration, KP108 did not affected animal health. Altogether, these are very encouraging data for future KP108 dose/safe/timely administration to patients, once moving to clinical trials with our compound.

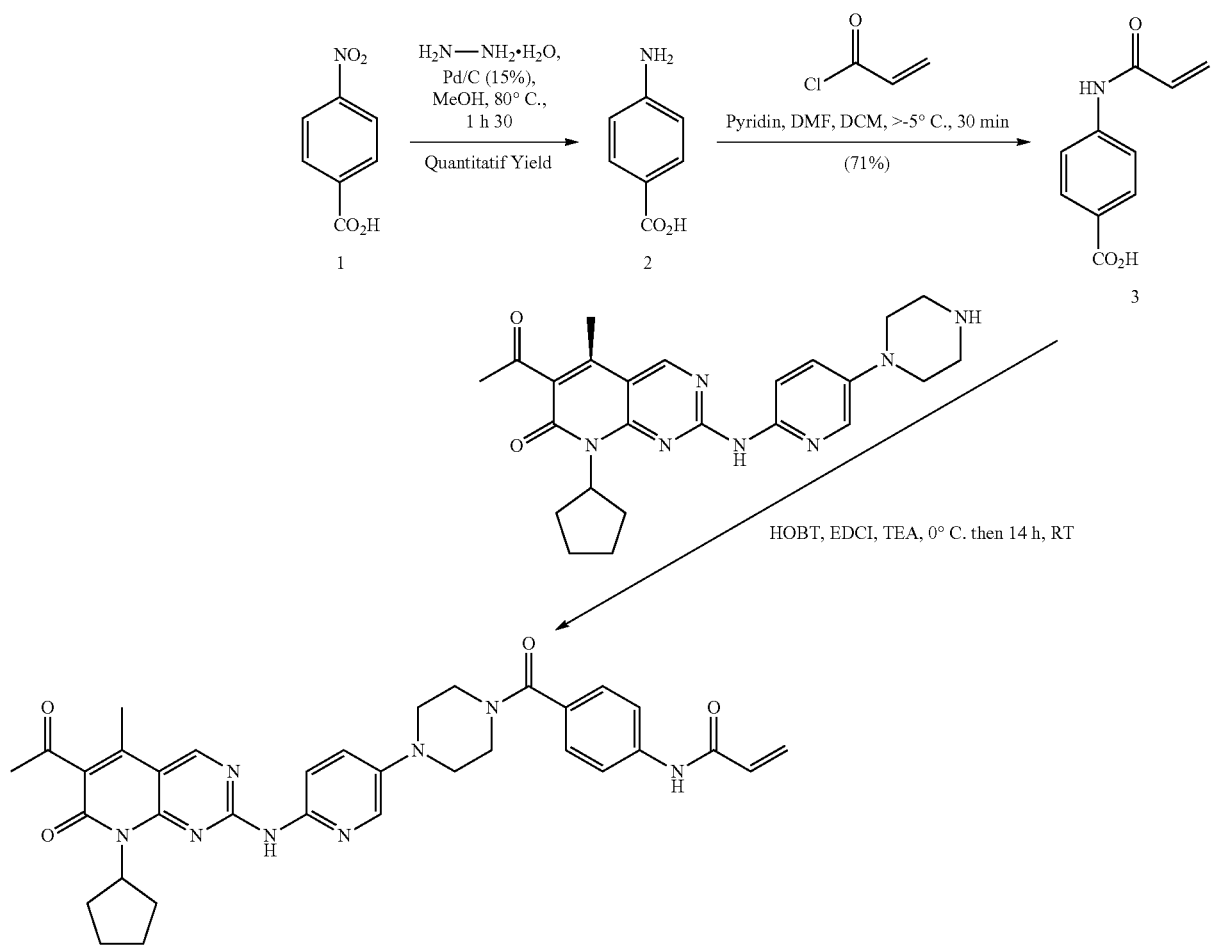

KP108

Material and Methods

Cell Culture: All the cell lines used were cultured at 37° C. in 5% CO2. HEK293T and MDA were maintained in Dulbecco's Modified Eagle Medium (DMEM) (Wisent Bio) with 10% fetal bovine serum (FBS) (Gibco). SUM159 was maintained in Ham's F-12 media with 5% FBS, 5 µg/mL insulin and 1 µg/mL hydrocortisone (Wisent Bio). HPAF-II was maintained in Eagle's Minimum Essential Medium (EMEM) (Wisent Bio) with 10% FBS. PC-3 was maintained in F-12K medium with 10% FBS.

CRISPR Knockout Plasmid Cloning: Single vector system LentiCRISPR V2 backbone (Addgene, plasmid #52961) was used to clone the non-targeting and targeting gRNA sequences for CDK4, CDK6. Cloning was performed as described in the addgene's protocol48. Three gRNAs for each gene were designed to target different genomic regions. Backbone vector was digested and dephosphorylated by BsmBI and FastAP (Fermentas) for 30 min at 37° C. The digested plasmid was gel-purified by QIAquick Gel Extraction Kit (Qiagen), The pair of oligos for each gene will be phosphorylated and annealed using T4 PNK enzyme in a thermocycler by incubating 30 min at 37° C. and 5 min at 95° C. and ramp down to 25° C. Annealed oligos were diluted at 1:200 and ligated together with digested vector using Quick ligase (NEB) for 20 min at room temperature. The cloned vectors were then transformed into Stbl3 bacteria (invitrogen).

Lentiviral Production and Infection: The HEK293T cell lines used were thawed and passaged according to the ATCC protocol. The cells were transfected for 12-16 hours at 37° C. using 15 µg cloned vector for each gene, 4.5 µg pMD2. G (Addgene 12259) and 12 µg psPAX2 (Addgene 12260). The medium was then changed with fresh complete medium DMEM with 10% FBS. After 24 hr virus production, the medium was collected and centrifuged at 1200 RPM for 5 mins to remove any cells in the medium and the supernatant (virus) was collected. SUM159 cells were thawed from frozen cells and were split into plates (50% confluent) and were cultured to attach overnight at 37° C. The cells were infected with 8 µg/mL of polybrene and 100 µL of virus for each plate and were left to incubate overnight. The medium was changed with fresh complete medium and was left to incubate for 24 hours. After incubating for 24 hours, 2 µg/mL puromycin was added to each plate. To establish stable cells, the cells underwent puromycin selection for at least 7 days.

Western Blot After washing the infected cells with ice-cold PBS twice, 300 µL of ice-cold cell lysis buffer (1M Tris-HCl, 5M NaCl, 10% Triton, 100 mM EDTA, 100 mM Na3VO4, ×100 Protease Inhibitor, 10× Phosphatase Inhibitor) was added to the dish. All the adherent cells were scraped off the dish and the cell suspension were transferred to a microcentrifuge tube. The cell suspension was left to incubated on ice for 10 min and the cell lysate mixture was centrifuge at 12,000 RPM for 20 mins at 4° C. The supernatant was transferred to a new microcentrifuge tube on ice. The protein concentration was determined using the BCA Kit (ThermoFisher). The lysate samples were diluted in 5×SDS Buffer and were heated at 95° C. for 5 min. The ladder and the samples were loaded into the wells of a SDS PAGE gel and the gel was then run at 100V. Following gel electrophoresis, a semi dry transfer was performed at 15V for 1.5 hours. The membranes were blocked in 5% milk for 1 hour at room temperature and was washed with TBS with 0.1% Tween 20 Buffer. The membrane was then incubated overnight at 4° C. with the primary antibodies (pRb. Total Rb). After incubating overnight, the membranes were washed and then incubated with goat anti-mouse or goat anti-rabbit immunoglobulin horseradish peroxidase conjugates (R&D systems suppliers/Millipore sigma) at a dilution of 1:3000 for 1 hour at room temperature. The membranes were washed and the ECL kit (Bio-Rad) was used to develop the membranes. The membranes were scanned using the ChemiDoc Touch Instrument (Bio-Rad).

In vitro growth inhibition assay: Growth inhibitory potency was evaluated using the SRB assay. Briefly, cells were plated in 96-well in triplicate and treated with drugs (0.0065 μM to 100 μM) 24 h after seeding. Following drug treatment, the cells were fixed using 50 μl of cold TCA (50%) for 1 h at 4° C., washed five times with tap water, and stained for 30 min at room temperature with SRB (0.4%) in acetic acid (0.5%). The plates were subsequently rinsed five times with acetic acid (1%) and allowed to air dry. The resulting purple residue was dissolved in Tris base (200 μl, 10 mM), and optical densities read on a ELx808 BioTek microplate reader. 1050 values were determined using the GraphPad Prism software.

Tumorsphere assays: Monolayer cells were enzymatically dissociated into single cells with trypsin-EDTA. Cells were plated at 10,000 cells per well in a 24-well low-attachment plate (Coming). Cells were grown for 7 days in DMEM/F12 supplemented with B27 (Invitrogen) in the presence of 10 ng/ml EGF and 10 ng/ml bFGF. Tumorsphere-forming efficiency was calculated as the number of spheres divided by the number of singles cells seeded, expressed as a percentage.

Apoptosis assay: Apoptotic rates were analyzed and quantified by flow cytometry following AnnexinV/PI staining on SUM159 and MDA-MB-468 breast cancer cells.

In vitro kinase profiling: To assess on-target and off-target kinase affinity and specificity of our lead inhibitor KP108 in a full kinome profiling, we will test the lead compound against Reaction Biology Corporation four panels (Wild Type. Panel (374 kinases), Mutant Panel (232 kinases), Atypical Panel (20 kinases), Lipid Panel (17 lipid kinases). This was outsourced to Reaction Biology Corporation, a biopharmaceutical company focused on the development of kinase inhibitors (http://www.reactionbiology.com/webapps/site/).

ALDEFLUOR assay was performed as described in the manufacturer's protocol, 1×106 SUM159 cells were centrifuged and resuspended in 1 ml ALDH assay buffer. 5 μl substrate was added into the cell suspension. For negative control, 500 μl cell suspension were then transferred into a new tube containing 5 μl DEAB. Cells were then incubated for 40 min at 37° C. Percentage of ALDH+ cells were analyzed with Accuri C6 flow cytometer and Flowjo software.

In vivo studies: All mice were housed and handled in accordance to the approved guidelines of the Canadian Council on Animal Care (CCAC) "Guide to the Care and Use of Experimental Animals" and under the conditions and procedures approved by the Animal Care Committee of McGill University (AUP #7497). The NSG mouse breeders were purchased from Jackson Laboratory (California, US). Female and male NSG mice between 7 and 9 weeks of age were bred and maintained in the animal facility of the Research Institute of the McGill University Health Center, as per the guidelines of the McGill University Animal Care Committee.

Xenograft model: Human breast cancer cells, SUM159 (1×106/mouse) were diluted in 1:1 with Matrigel and then inoculated in 8-week old, female NSG mice by mammary fat pad route to generate breast cancer tumor. Tumor sizes were measured with a digital electronic caliper three times per week to reach maximum volume of 1000 mm3 prior to euthanasia. Tumor volumes were calculated according to the following formula: [4/3×π×(Length/2)×(Width/2)2] to generate a growth curve.

Intravenous injection model: cells (1×106/each) were injected by tail vein route to develop lung metastases. The mice were euthanized with a maximum of 42-day (SUM159) post cancer cells injection. The lung tissues were counted for metastases nodules post Bouin's solution fixation.

4-aminobenzoic acid. m/z: 138.0477. To a cooled solution of 4-nitrobenzoic acid 1 (18 mmol), Pd/C (15% molaire) in MeOH (30 mL) at 0° C., was added slowly hydrazine monohydrate (180 mmol), the reaction is highly exothermic. The mixture was warmed to 80° C. and stirred for 1h30. Then the reaction mixture was cooled to room temperature and filtered on celite pad. The cake was washed with MeOH (2×10 mL) and the filtrate was concentrated. The crude material was triturated in Hexane/Acetone (2:1), filtered and concentrated to afford the pure compound 2. White product; yield quantitative. $^1$H NMR (400 MHz, CDCl$_3$) δ 7.86 (d, J=8.5 Hz, 2H), 6.66 (d, J=8.5 Hz, 2H). $^{13}$C NMR (101 MHz, DMSO-d$_6$) δ 167.60, 163.17, 131.31, 117.01, 112.66.

4-acrylamidobenzoic acid m/z: 192.0582 (100.0%), 192.0616 (10.8%). To a cooled solution (<−5° C.) of 2 (7.3 mmol), pyridine (4.4 mmol) in DMF (3 mL), was added a solution of acryloyl chloride (7.3 mmol) in DCM (2 mL) with dropwise manner. At the end of addition, the resulting mixture was keeping under −5° C. and stirred for 30-45 min until the end of reaction, which was monitored by TLC. The reaction mixture was poured into ice water (100 mL). The precipitated product was filtered and dried to afford pure compound 3. White powder; yield 71%. $^1$H NMR (400 MHz, CDCl$_3$) δ 12.68 (s, 1H), 10.44 (s, 1H), 7.91 (d, J=8.6 Hz, 1H), 7.78 (d, J=8.6 Hz, 1H), 6.47 (dd, J=17.0, 10.0 Hz, 1H), 6.30 (dd, J=17.0, 1.8 Hz, 1H), 5.81 (dd, J=10.0, 1.8 Hz, 1H). $^{13}$C NMR (101 MHz, DMSO-d$_6$) δ 166.86, 163.50, 143.02, 131.57, 130.38, 127.64, 125.36, 118.47.

N-(4-(4-(6-((6-acetyl-8-cyclopentyl-5-methyl-7-oxo-7,8-dihydropyrido[2,3-d]pyrimidin-2-yl)amino}pyridin-3-yl) piperazine-1-carbonyl)phenyl)acrylamide (KNOB) m/z: 621.2942. To a cooled mixture of Palbociclib (1.56 mmol.), 4-acrylamidobenzoic acid (1.72 mmol), 1-hydroxybenzothriazol (HOBt, 1.87 mmol) and triethylamine (1.72 mmol.) in dimethylformamide (DMF, 5 mL) under argon at 0° (ice bath), was added dropwise 1-ethyl-3-[3-(dimethylamino) propyl]carbodiimide (EDCl, 1.72 mmol.). At the end of the addition, the resulting mixture was warmed to room temperature and stirred for 10-15 h until the end of reaction, which was monitored by TLC. After the completion of reaction, the reaction mixture was poured into water and the resulting precipitated was filtered and washed with water. The crude material was purified by silica gel chromatography (dichloromethane/methanol) to afford pure compounds. Yellow solid; yield 88%. $^1$H NMR (400 MHz, CDCl$_3$) δ 9.43 (bs, 1H), 8.92 (s, 1H), 8.56 (s, 1H), 8.20 (d, J=9.0 Hz, 1H), 8.14 (bs, 1H), 7.61 (d, J=8.3 Hz, 2H), 7.37 (d, J=8.3 Hz, 2H), 7.36 (m, 1H), 6.44 (d, J=16.6 Hz, 1H), 6.32 (dd, J=16.6, 10.1 Hz, 1H), 5.97-5.80 (m, 1H), 5.74 (d, J=10.1 Hz, 1H), 3.82 (bs, 4H), 3.19 (bs, 4H), 2.54 (s, 3H), 2.42 (s, 3H), 2.34-2.22 (m, 2H), 2.10-1.95 (m, 2H), 1.88-1.76 (m, 2H), 1.72-1.60 (m, 2H). $^{13}$C NMR (101 MHz, CDCl$_3$) δ 202.67, 170.20, 163.98, 161.35, 158.09, 157.29, 155.52, 145.95, 143.00, 141.79, 139.82, 137.09, 130.96, 130.67, 130.59, 128.15, 126.97, 119.94, 113.55, 107.57, 54.17, 50.05, 31.51, 28.02, 25.68, 13.94. HPLC purity: 97.69%, $^1$R=6.30 min. HR MS (ESI) m/z: calcd [C34H36N8O4+H]$^+$621, 2860, found 621.2942.

REFERENCES

1. Bianchini, G., Balko, J. M., Mayer, I. A., Sanders, M. E. & Gianni, L. Triple-negative breast cancer: challenges and opportunities of a heterogeneous disease. *Nature Reviews Clinical Oncology* 13, 674, doi:10.1038/nrclinonc.2016.66 (2016).
2. Prager, B. C., Xie, Q., Bao, S. & Rich, J. N. Cancer Stein Cells: The Architects of the Tumor Ecosystem. *Cell Stem Cell* 24, 41-53, doi:10.1016/j.stem.2018.12.009 (2019).
3. Nagini, S. Breast Cancer: Current Molecular Therapeutic Targets and New Players. *Anticancer Agents Med Chem* 17, 152-163 (2017).
4. Reya, T., Morrison, S. J., Clarke, M. F. & Weissman, I. L. Stem cells, cancer, and cancer stem cells. *Nature* 414, 105-111, doi:10.1038/35102167 (2001).
5. Thomas, M. L., Coyle, K. M., Sultan, M. & Marcato, P. in *Cancer Stem Cells: Emerging Concepts and Future Perspectives in Translational Oncology* 477-518 (Springer, 2015).
6. Dai, M. et al. CDK4 regulates cancer sternness and is a novel therapeutic target for triple-negative breast cancer. *Sci Rep* 6, 35383, doi:10.1038/srep35383 (2016).
7. Turner, N. C. et al. Palbociclib in Hormone-Receptor-Positive Advanced Breast Cancer. *The New England journal of medicine* 373, 209-219, doi:10.1056/NEJMoa1505270 (2015).
8. Jeong, S. B. et al. Essential Role of Polo-like Kinase 1 (Plk1) Oncogene in Tumor Growth and Metastasis of Tamoxifen-Resistant Breast Cancer. *Mol Cancer Ther* 17, 825-837, doi:10.1158/1535-7163.MCT-17-0545 (2018).
9. Fu, Z. & Wen, D. The Emerging Role of Polo-Like Kinase 1 in Epithelial-Mesenchymal Transition and Tumor Metastasis. *Cancers (Basel)* 9, doi:10.3390/cancers9100131 (2017).
10. Dai, M. et al. Differential regulation of cancer growth and metastasis by CDK4 and CDK6 highlighting a central role for the DNA replication pathway. *Cancer Cell*, submitted (2019).
11. Tian, J. et al. Cyclooxygenase-2 regulates TGFbeta-induced cancer sternness in triple-negative breast cancer. *Sci Rep* 7, 40258, doi:10.1038/srep40258 (2017).
12. Lopez-Ozuna, V. M., Hachim, L Y., Hachim, M. Y., Lebrun, J. J. & Ali, S. Prolactin Pro-Differentiation Pathway in Triple Negative Breast Cancer: Impact on Prognosis and Potential Therapy. *Sci Rep* 6, 30934, doi: 10.1038/srep30934 (2016).
13. López-Ozuna V M, H. I., Hachim M Y, Lebrun J J, Ali S. Prolactin modulates TNBC aggressive phenotype limiting tumorigenesis. *Endocr Relat Cancer*. ERC-18-0523.R1. doi: 10.1530/ERC-18-0523. [Epub ahead of print] (2019).
14. Stefansson, O. A. et al. CpG island hypermethylation of BRCA1 and loss of pRb as co-occurring events in basal/triple-negative breast cancer. *Epigenetics* 6, 638-649, doi:10.4161/epi.6.5.15667 (2011).
15. Treré, D. et al. High prevalence of retinoblastoma protein loss in triple-negative breast cancers and its association with a good prognosis in patients treated with adjuvant chemotherapy. *Annals of Oncology* 20, 1818-1823, doi:10.1093/annonc/mdp209 (2009).
16. Dai, M. et al. A novel function for p21Cip1 and acetyl-transferase p/CAF as critical transcriptional regulators of TGFbeta-mediated breast cancer cell migration and invasion. *Breast Cancer Res* 14, R127, doi:10.1186/bcr3322 (2012).
17. Dai, M. et al. Cyclin D1 cooperates with p21 to regulate TGFbeta-mediated breast cancer cell migration and tumor local invasion. *Breast Cancer Res* 15, R49, doi:10.1186/ber3441 (2013).
18. Liu, T. et al. CDK4/6-dependent activation of DUBS regulates cancer metastasis through SNAIL1. *Nat Commun* 8, 13923, doi:10.1038/ncomms13923 (2017).
19. Tian, J. et al. Dasatinib sensitises triple negative breast cancer cells to chemotherapy by targeting breast cancer stem cells. *Br J Cancer* 119, 1495-1507, doi:10.1038/s41416-018-0287-3 (2018).

What is claimed is:

1. A molecule of Formula I or a pharmaceutically acceptable salt thereof:

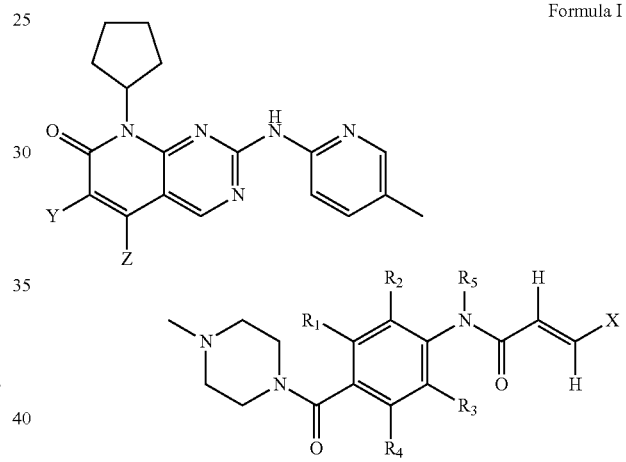

Formula I wherein:

R1 is selected from a group consisting of H, F, Cl, Br, CN, NO$_2$, Me

R2 is selected from a group consisting of H, F, Cl, Br, CN, NO$_2$, Me

R3 is selected from a group consisting of H, F, Cl, Br, CN, NO$_2$, Me

R4 is selected from a group consisting of H, F, Cl, Br, CN, NO$_2$, Me

R5 is selected from a group consisting of H, Me, Et, Propyl

X is selected from a group consisting of H, Me, —CH2=CH2-CH3, —(CH$_2$)$_n$—N(CH$_3$)$_2$,

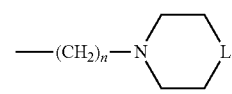

where n=1, 2, 3, 4 L=O, NH, NMe,

Y is selected as CH3CO or CN

Z is selected from H or Me.

2. A molecule as per claim 1 where Y=CH3CO, Z=H, R1=R2=R3=R4=R5=H and X=H.

3. A molecule of Formula II or a pharmaceutically acceptable salt thereof:

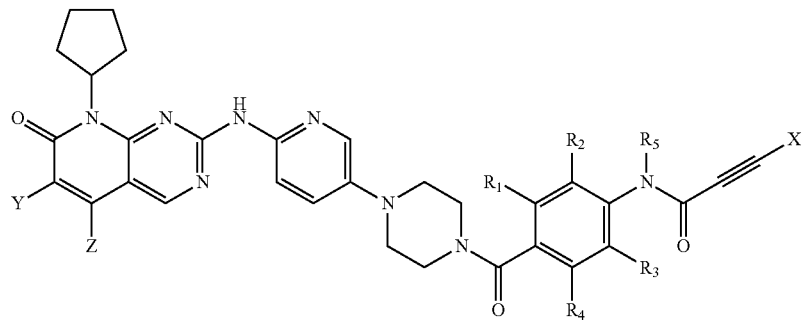

Formula II wherein:

R1 is selected from a group consisting of H, F, Cl, Br, CN, NO$_2$, Me

R2 is selected from a group consisting of H, F, Cl, Br, CN, NO$_2$, Me

R3 is selected from a group consisting of H, F, Cl, Br, CN, NO$_2$, Me

R4 is selected from a group consisting of H, F, Cl, Br, CN, NO$_2$, Me

R5 is selected from a group consisting of H, Me, Et, Propyl

X is selected from a group consisting of H, Me, —(CH$_2$)$_n$—N(CH$_3$)$_2$

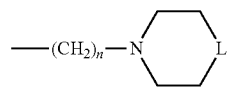

where n=1, 2, 3, 4 L=O, NH, NMe,

Y is selected as CH3CO or CN

Z is selected from H or Me.

4. A molecule of Formula III or a pharmaceutically acceptable salt thereof:

wherein:

R1 is selected from a group consisting of H, F, Cl, Br, NO$_2$, Me

R2 is selected from a group consisting of H, F, Cl, Br, NO$_2$, Me

R3 is selected from a group consisting of H, F, Cl, Br, NO$_2$, Me

R4 is selected from a group consisting of H, F, Cl, Br, NO$_2$, Me

R5 is selected from a group consisting of H, Me, Et, Propyl

X is selected from a group consisting of H, Me, —(CH$_2$)$_n$—N(CH$_3$)$_2$

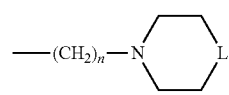

where n=1, 2, 3, 4 L=O, NH, NMe,

Y is selected as CH3CO or CN

Z is selected from H or Me.

Formula III

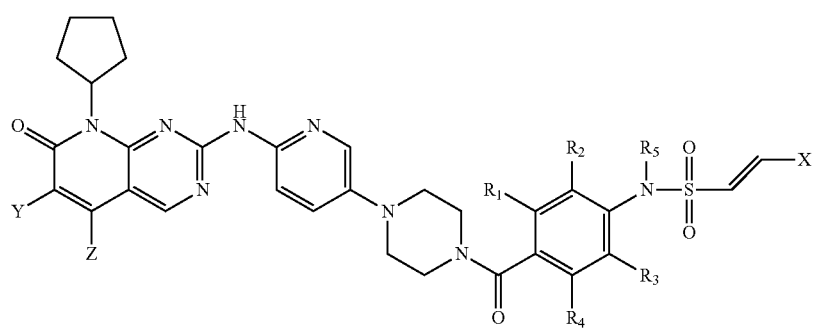

5. A molecule of Formula IV or a pharmaceutically acceptable salt thereof,

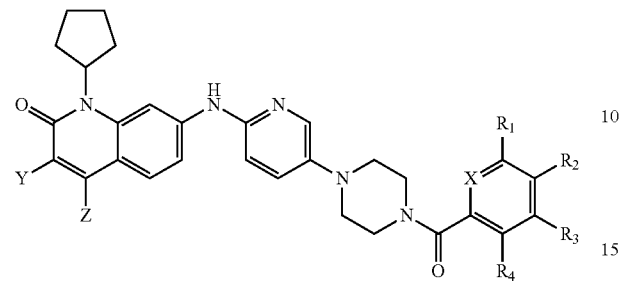

Formula IV wherein:
R1 is selected from a group consisting of H, F, Cl, Br, CN, NO$_2$, Me,

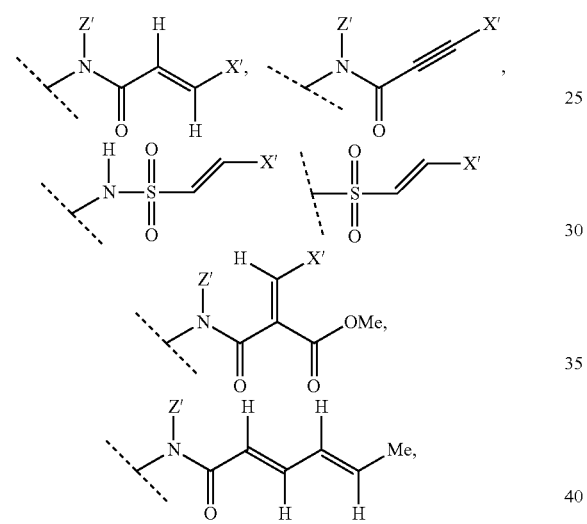

R2 is selected from a group consisting of H, F, Cl, Br, CN, NO$_2$, Me,

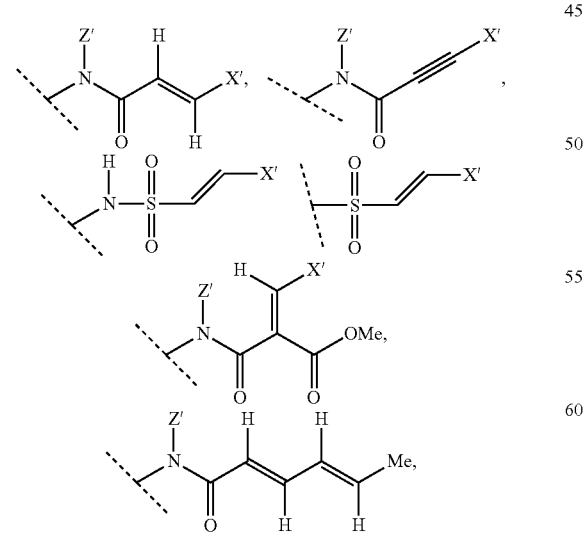

R3 is selected from a group consisting of H, F, Cl, Br, CN, NO$_2$, Me

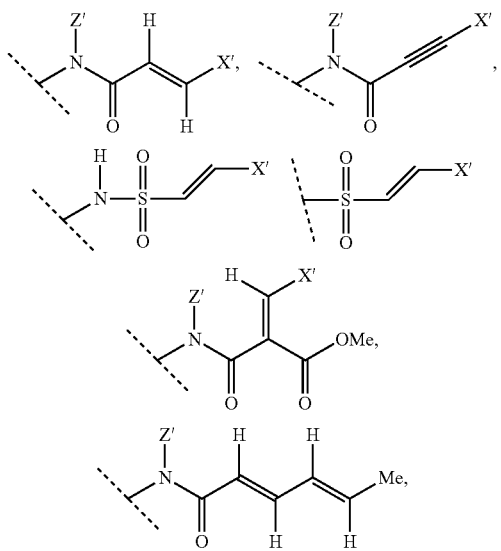

R4 is selected from a group consisting of H, F, Cl, Br, CN, NO$_2$, Me

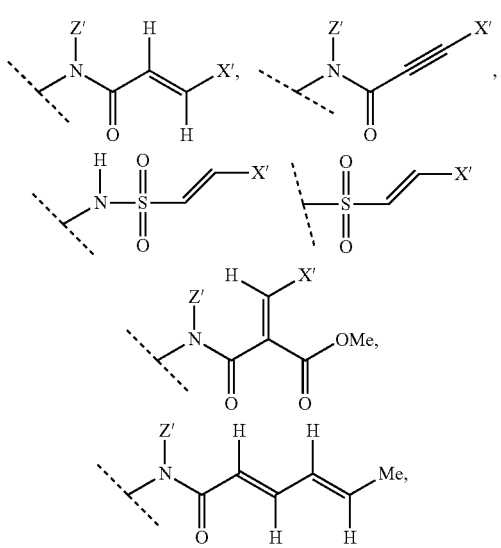

X is selected as C or N

X' is selected from a group consisting of H, Me, —(CH$_2$)$_n$—N(CH$_3$)$_2$

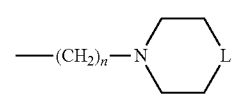

where n=1, 2, 3, 4 L=O, NH, NMe,

Z' is selected from consisting of H or Me

Y is selected as CH3CO or CN

Z is selected from H or Me.

6. A method of treating human with tumors in the breast, pancreas, prostate, and lung, and comprising and administering a therapeutically effective amount of a molecule as defined in any one of claims 1 to 5.

7. A pharmaceutical composition comprising a molecule as defined in any one of claims 1 to 5 and a pharmaceutically acceptable carrier.

8. A method of eradicating human tumor initiating cells in solid tumors in the breast, pancreas, prostate, and lung with a single molecule as defined in claim 2, targeted to CDK4, CDK6 and PLK1.

9. A pharmaceutical composition comprising a molecule as defined in any one of claims 1 to 5 in combination with one or more pharmaceutically acceptable diluents or excipients.

* * * * *